United States Patent [19]

Pelka et al.

[11] 4,448,545

[45] May 15, 1984

[54] NON-INTRUSIVE THERMAL POWER MONITOR AND METHOD

[75] Inventors: David G. Pelka; Roc V. Fleishman, both of Los Angeles, Calif.

[73] Assignee: Southern California Gas Company, Los Angeles, Calif.

[21] Appl. No.: 354,012

[22] Filed: Mar. 2, 1982

[51] Int. Cl.³ .......................................... G01K 17/16
[52] U.S. Cl. .................................................... 374/41
[58] Field of Search .................... 73/204; 364/510; 374/39-41

[56] References Cited

U.S. PATENT DOCUMENTS

| | | | |
|---|---|---|---|
| 2,729,976 | 1/1956 | Laub | 73/204 |
| 2,960,914 | 12/1959 | Graves | 73/204 X |
| 3,438,254 | 4/1969 | Seeley | 73/204 |
| 3,500,686 | 3/1970 | Bell | 73/204 |
| 3,724,261 | 4/1973 | Kydd | 374/36 |
| 4,224,825 | 9/1980 | Feller | 374/41 |
| 4,244,217 | 1/1981 | Ledbetter | 73/204 |

FOREIGN PATENT DOCUMENTS 1353322 5/1974 United Kingdom .................. 374/41

Primary Examiner—Herbert Goldstein
Attorney, Agent, or Firm—Christie, Parker & Hale

[57] ABSTRACT

A non-intrusive thermal power monitor and method for determining the amount of sensible heat withdrawn from or added to a fluid stream flowing in a conduit by an unknown source includes a thermal power transfer device that supplies or removes a known amount of heat energy to the fluid in a conduit. First and second temperature sensors sense the temperature of the fluid stream across the thermal power transfer device, and this information is used to determine a heat capacity rate of the fluid in the fluid stream. Additional non-intrusive temperature sensors sense the temperature of the fluid stream as it passes through and across a thermal power sink or heat source and provides a temperature differential. These temperatures are processed in a control circuit, and the thermal power added to or extracted from the fluid stream is determined in the control circuit by multiplying the measured temperature differential by the heat capacity rate of the fluid stream.

30 Claims, 6 Drawing Figures

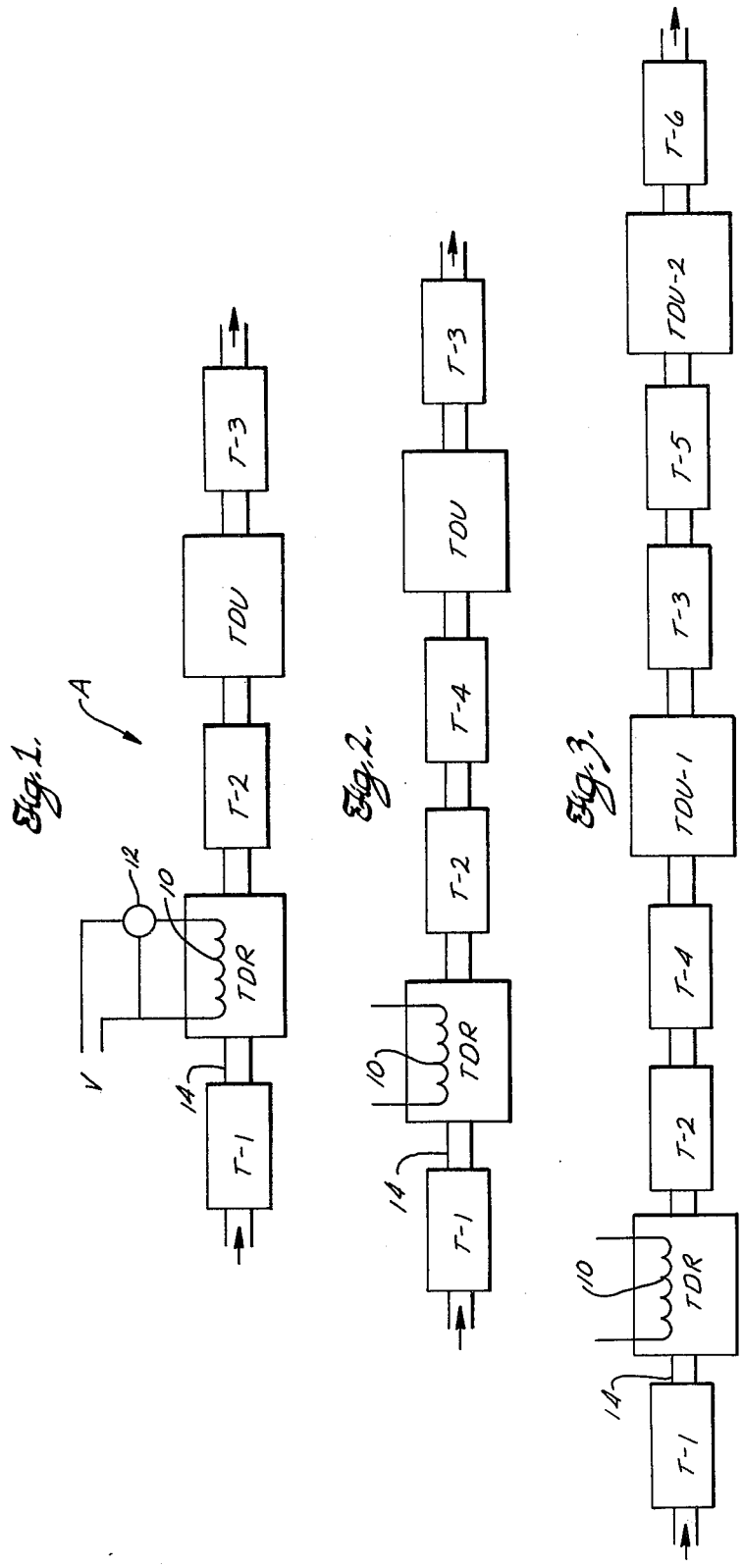

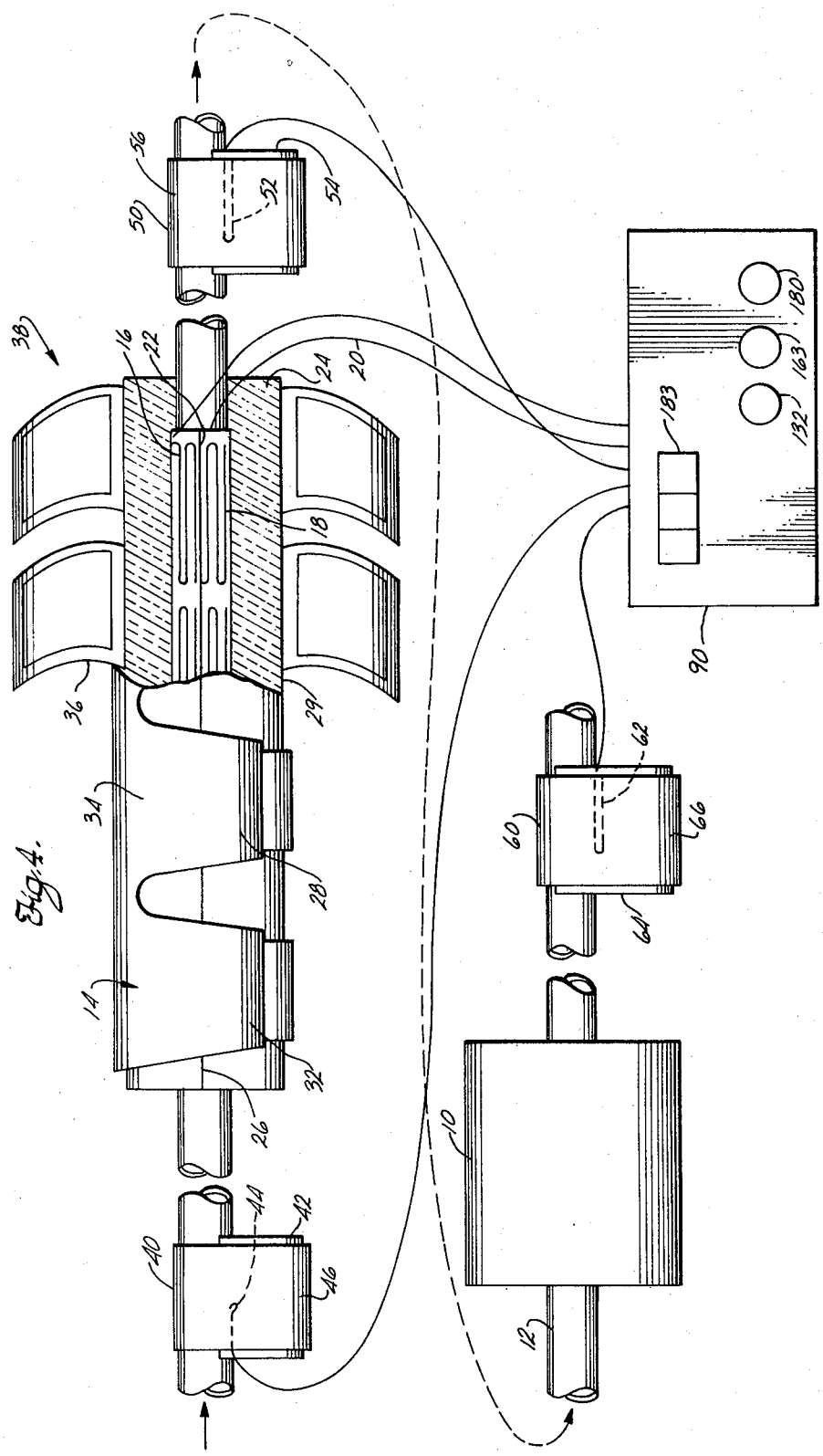

NON-INTRUSIVE THERMAL POWER MONITOR AND METHOD

BACKGROUND OF THE INVENTION

This invention relates to an apparatus and method for monitoring the amount of thermal power added to or withdrawn from a moving fluid stream, and more specifically, to a non-intrusive apparatus and method which measures the amount of thermal power input or extraction from a flowing fluid by determining the sensible heat capacity rate of the fluid and a temperature differential resulting from the thermal power input or extraction.

There has long been an interest in determining rapidly, economically and easily the thermal power contribution to a flowing stream of fluid from an unknown source, or the thermal power extraction from the fluid stream by an unknown thermal power sink. A myriad of industrial and residential systems employ flowing fluid to which thermal power is either added or taken away. It is quite useful to know the amount of that thermal power added to or extracted from the fluid for determining system efficiencies, losses and capabilities. Thermal energy, which is thermal power multiplied by time, may be considered of more fundamental interest; thermal power and thermal energy are related through the time parameter and can readily be derived from each other.

There are various types of devices used for determining thermal power input into a fluid stream. These devices have tended to be relatively expensive and for that reason are of limited utility.

These prior art devices include intrusive systems. One such system is a null system. In the null system, temperatures upstream and downstream from the unknown source of energy are taken. A heater supplies energy into the stream and the temperatures upstream and downstream of the heater are taken. The energy input of the heater is adjustable to vary the temperature difference upstream and downstream of the heater to equal the temperature difference across the unknown source. When these two temperature differences are the same, the amount of thermal energy introduced into the stream by the heater equals the energy introduced into the system from the unknown source. A null system is comparatively expensive. Null systems also can use too much energy; for example, when the temperature difference across the unknown source is high, a large amount of energy is required to produce the same temperature differential across the heater. Also, when the flow rate is high, a large amount of energy may also be required from the heater to achieve the same temperature differential across the heater. Null systems may also require considerable peak power capacity to enable them to monitor transients, such as a blowdown of a hot storage tank. The large power requirements of a null system can require an intrusive heater, one that is physically in the stream being monitored and not outside the stream's conduit. Null systems can result in or necessitate undesirable alterations in the stream being monitored and complicating procedures. For example, when a large amount of heat energy must be introduced into the stream, it may be necessary to cool the stream to prevent boiling. With high energy input, if heat input is not carefully controlled, the fluid could change state and boil. Further, cooling and then heating the stream results in considerable heat utilization. Null systems also require continual adjustments resulting in complex electronics.

One specific form of null system is disclosed in U.S. Pat. No. 2,398,606 to C. C. Wang, which is specifically designed for ultra-high frequency power measurement. In this particular system, constant temperature ratios are imperative for accuracy.

Intrusive systems, such as the null system, require breaking into the line carrying the fluids. Breaking into the line is clearly a disadvantage.

Heat meters are also in the prior art. One representative of heat meter is described in U.S. Pat. No. 3,167,957 to Ziviani in which heat transferred from a fluid is measured. In Ziviani, an intrusive by-pass duct removes a constant fraction of the fluid from a main stream. This constant fraction is heated in the by-pass duct to a temperature that is a specified function of the amount of heat removed from the fluid in the overall system. The Ziviani patent relies on a flow rate restriction in the main stream which could result in scale build-up in a relatively short period of time.

There are substantial problems with heat meters of this type. A major problem is the necessity to divert fluid and to heat the diverted fluid in proportion to the amount of heat withdrawn by the overall system. It is also exceedingly difficult to obtain a constant fraction of a fluid. In addition, devices of this type use thermocouples which are inherently non-linear. Systems of this type are intrusive because temperature sensors are in the fluid and the by-pass duct must be connected to the main stream for diversion of that stream.

Another heat measuring device is taught in U.S. Pat. No. 2,931,222 to Noldge et al. A fraction of a fluid previously cooled in a heat exchanger is heated to its original temperature. With knowledge of the fraction, the specific heat of the fluid, and the temperature increase, the amount of heat energy taken from the fluid is readily determined. This device is similar to a null system except that it operates in reverse and only on a fraction of the fluid. The system has many disadvantages including the fact that the inlet temperature of the fluid must be known. Further, systems of this type to be accurate must avoid corrosion or scale build-up, and fluid properties, such as viscosity and density, and flow rate, must remain the same; thus, if the viscosity or the flow rate of the fluid changes, the system becomes inaccurate.

U.S. Pat. No. 3,802,264 to Poppendiek et al discloses a meter to determine the flow rate of a stream and utilizes a heater to heat the fluid stream and measures the stream temperature increase. Temperatures are not measured at or beyond the upstream and downstream ends of the power input, but rather intermediate the ends of the power input. In other words, the system of this patent monitors temperature before the heat is uniformly distributed throughout the fluid. With the temperature increase and the power input, the flow rate allegedly can be determined.

Thermally operated flow meters of the type taught in Poppendiek et al are necessarily restricted to laminar flow operation in order to maintain required linearity. Further, the fluid must be homogeneous and it is necessary to know or to be able to derive the specific heat of the fluid. Also, other properties of the fluid, such as density, viscosity and thermal conduction, significantly affect the accuracy, necessitating calibration for each fluid type and input temperature. Consequently, such devices are rather limited in use and in application.

Hot wire anemometry is still another approach for measuring fluid flow. Here, a wire in the stream has power supplied to it. Heat from the wire transfers to the stream. The rate at which heat is lost from the wire is a non-linear measure of stream velocity. The disadvantages of hot wire anemometry include its intrusive character and non-linear output. Hot wire anemometry also depends upon a measure of total heat transfer from the wire and not a measure of a predetermined amount of heat transfer. In other words, hot wire anemometry determines how much heat transfer occurs and does not measure the result of a heat transfer, i.e., temperature change.

A publication entitled "Analog Devices, Multiplier Application Guide," by James Williams et al of Analog Devices, Inc. (1978), teaches a thermally operated flow meter for measuring fluid flow rate. A length of pipe is inserted into or connected to a line carrying the fluid. The pipe includes a resistive heater and upstream and downstream intrusive temperature measuring probes. This device is effective only for measurement of very slow flow rates and requires complex circuitry to enable a constant amount of heat to be supplied to the fluid stream. The device further includes screens located in the pipe or elsewhere in the flow stream to mix the fluid and enhance temperature measurement accuracy.

Flow meters which operate on thermal principles, such as the device in the Poppendiek et al patent, are adapted only for measuring the flow rate of a fluid and are not capable of measuring an amount of heat added to or extracted from a fluid by an unknown heat source or heat sink.

SUMMARY OF THE INVENTION

The present invention provides a non-intrusive heat monitor and method to measure the thermal energy or thermal power input or withdrawal from a flowing fluid in a relatively inexpensive, efficient, and easy manner. More specifically, the present invention provides a non-intrusive apparatus and method which measures the amount of thermal power withdrawn from or added to a flowing fluid by using a determined sensible heat capacity rate of the fluid stream.

The monitor of the present invention includes a non-intrusive thermal power transfer device capable of adding or removing a known or measurable amount of heat to a fluid stream flowing through a fluid carrying conduit. The thermal power transfer device may be a heater, for example, an electrically resistive heater. The heat transfer device may be a heat sink, for example, a refrigerator system. While either can be used, the heater is often preferred. This power transfer device is a reference thermal power transfer device because it determines a reference signal. A first temperature differential sensing means adapted to measure a first temperature differential across the thermal power transfer device determines the temperature change in the fluid due to the heat added to or removed from the fluid stream by the transfer device. The first temperature differential sensing means includes a pair of non-intrusive temperature sensors for location across the thermal power transfer device. A second temperature differential sensing means of one or more temperature sensors senses the temperature across an unknown heat source or heat sink. The first temperature differential temperature sensing means, along with the reference power transfer device, determines the heat capacity rate of the fluid in the flowing fluid stream.

The temperature measurements which give rise to the temperature differentials are preferably converted in a converter to electrical signals which are functions of the measured temperature differentials. More specifically, these electrical signals are proportional to the measured temperature differential, although they do not have to be linearly proportional. They can be frequency or digital representations of the measured temperature differential, or analog, and a function of temperature. Means determine the heat capacity rate of the fluid in the fluid stream from the temperatures provided by the first temperature differential means. Means multiply the temperature differentials across the unknown sources or sinks by the determined heat capacity rate of the fluid. This results in a determination of the amount of heat (or thermal power) which has been added to or withdrawn from the fluid stream by the one or more unknown heat sources or heat sinks. The result can be used to control a function, as for example, control the unknown source or provide control over the thermal reference device.

The direction of fluid flow with respect to the reference thermal power transfer device and the one or more unknown heat sinks or heat sources is not critical to the invention, although temperature differentials must be taken in a consistent direction, for example, from upstream to downstream or downstream to upstream. The unknown heat sources or unknown heat sinks, if more than one, may be located on different sides of the reference thermal power transfer device.

The monitor and method are primarily operable with a series fluid stream. That is, the thermal power transfer device, the unknown source or sink, and associated sensors operate on the same stream and not on parallel streams.

In a more detailed embodiment of the invention, the thermal power transfer device is an electrically operable heater with a constant electrical resistance so that the amount of heat generated is proportional to the square of the current or voltage used to provide this heat. In addition, the energy in the amount of heat applied to the fluid, with negligible loss, is substantially equal to the energy in the electrical power consumed to generate that heat. This current, or voltage, or electrical power provides a measure of the amount of heat applied and is processed in a circuit to determine the heat capacity rate of the fluid in the fluid stream and also to enable measurement of the amount of heat added to or removed from the fluid stream by the unknown heat source or heat sink.

In a preferred form, the heater includes a heater element of alloy wire in a silicone sheet. This heater is jacketed in an insulation, say, of silicone foam. A sleeve encases the insulation and has means for attaching the entire unit to a pipe through which the fluid to be monitored passes. Such attachment means might be in the form of hook and pile fastening strips. A radiation shield encapsulates the insulation sleeve. The temperature sensors are themselves insulated to avoid environmental influences. They are also attachable to the line as by some fastener means such as hook and pile fasteners.

The temperature sensors should be fairly sensitive, preferably to within about 0.001 degrees Celsius to minimize necessary reference temperature difference to achieve system accuracy. It has been found that to avoid effects of heat conduction on the pipe and poor thermal mixing on the accuracy of the instrument, it is desirable to observe a point of attachment upstream and downstream of the thermal power transfer device of at least 10 and preferably 20 pipe diameters for the temperature sensors. This spacing criteria is especially desirable downstream from the reference heat transfer device. The same spacing is important downstream of the unknown thermal power sources or sinks unless it is known that the fluid is well mixed at that point.

"Heat capacity rate" is the amount of energy added or withdrawn from a stream per unit time per unit temperature change in the stream.

The term "heat contribution" or the term "thermal power contribution" refers to that amount of heat or thermal power which is either added to or removed from the fluid stream, the term "contribution" being used in both a positive sense when thermal power is added and a negative sense when thermal power is withdrawn from the fluid stream.

These and other features, aspects and advantages of the present invention will become more apparent from the following description, appended claims and drawings.

BRIEF DESCRIPTION OF THE DRAWINGS

FIG. 1 is a schematic block diagram illustrating one arrangement of a thermal power monitor constructed in accordance with the present invention in relation to an unknown thermal power source or sink;

FIG. 2 is a schematic block diagram illustrating another arrangement of a thermal power monitor constructed in accordance with the present invention in relation to an unknown thermal power source or sink using different temperature sensor arrangements;

FIG. 3 is a schematic block diagram illustrating another arrangement of a thermal power monitor constructed in accordance with the present invention in relation to a plurality of unknown thermal power sources or sinks;

FIG. 4 illustrates somewhat schematically a preferred form of the thermal power monitor of the present invention;

DESCRIPTION OF THE PREFERRED EMBODIMENTS

Figure 5:
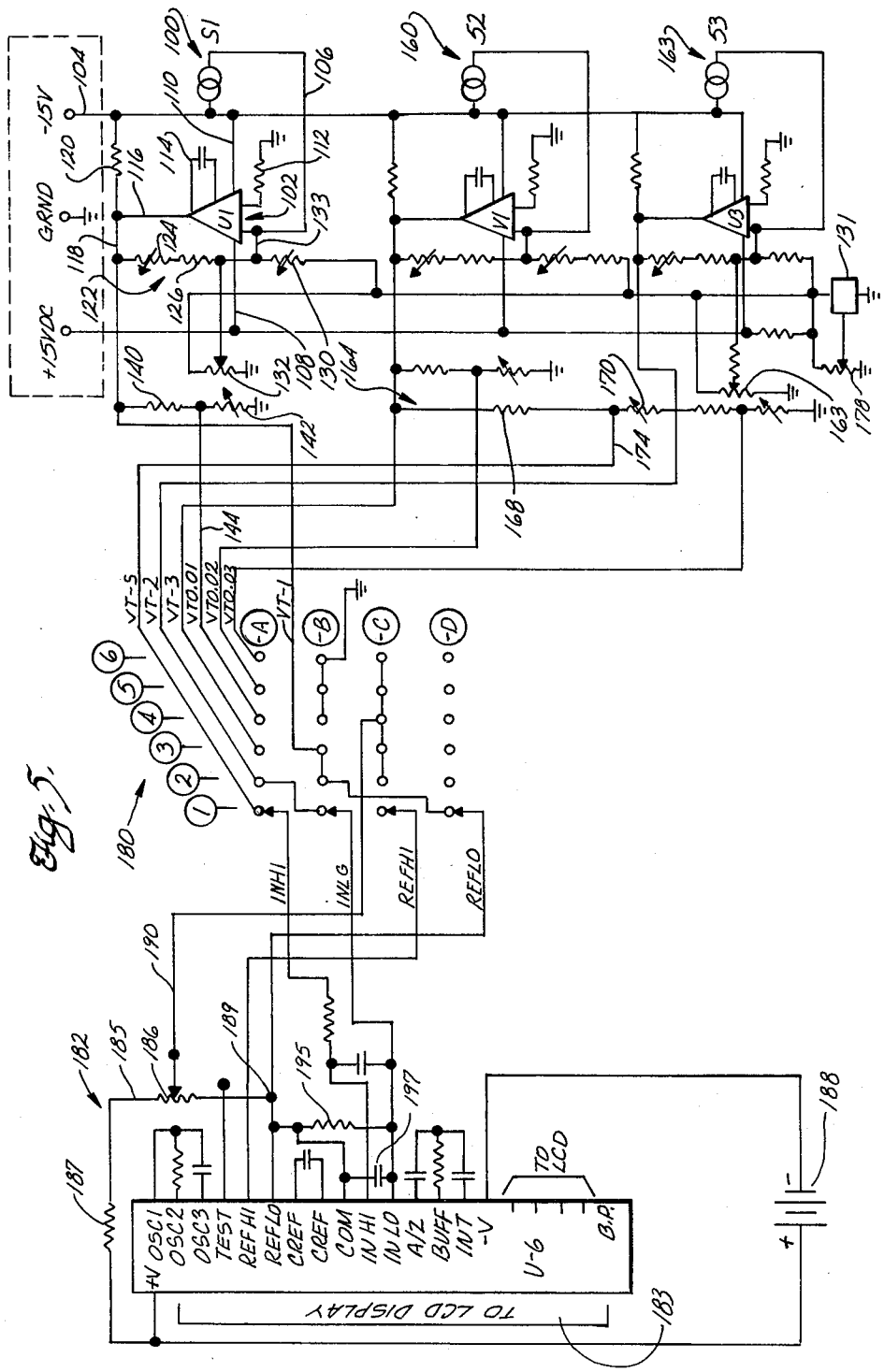
FIG. 5 is a schematic electrical circuit for the invention embodiment of FIG. 4.

FIG. 1 illustrates in a simple schematic block diagram form a thermal power monitor designated by reference letter "A" for monitoring an unknown thermal power sink or an unknown thermal power source, designated as TDU. Monitor "A" comprises a reference thermal power device TDR. In the preferred form, the reference thermal power device is a heater which applies a known or measurable amount of heat to a fluid stream. However, a cooling device which withdraws a known or measurable amount of heat from the fluid stream can be employed as the reference thermal power device. In the specific embodiment shown in FIG. 1, thermal reference device TDR has an electrical resistive element 10 and and a power meter 12 connected to the resistiveelement for measuring the amount of electrical power delivered to element 10 and provides a measure of the amount of heat supplied to a fluid stream.

In the embodiment illustrated in FIG. 1, a fluid stream is carried in a conduit 14. Thermal reference device TDR is disposed outside conduit 14 in thermal communication with it. The thermal reference device does not intrude into the fluid stream.

Thermal power monitor "A" also utilizes a first temperature differential measuring means including a first temperature sensor T-1 on one side of the thermal reference device TDR and a second temperature sensor T-2 on the opposite side of the thermal reference device TDR, in the manner illustrated. In this way, a first temperature differential across the temperature reference device can be measured which is used to determine the heat capacity rate of the fluid in the fluid stream, as described below.

The thermal power monitor includes a second heat differential measuring means in the form of a third temperature sensor T-3 located on the downstream side of heat sink or heat source TDU. The third temperature sensor cooperates with the second temperature sensor T-2. Sensors T-2 and T-3 are designed to measure the amount of heat added to or withdrawn from the fluid stream by the unknown source or unknown sink TDU.

For purposes of understanding the theory of operation, assume that the thermal reference device is a heater. If the rate of heat input, dQR, into the fluid across the thermal power device TDR is known or measurable, then the rate of heat input or the rate of heat withdrawal, dQU, across the unknown heat sink or heat source can be determined.

By measuring the temperature differential across reference thermal power device TDR, it is possible to determine the heat capacity rate. Heat capacity rate "C" is the amount of energy added or withdrawn from a stream per unit time per unit temperature change in the stream, (for example, Btu/hr/° F.). In essence the heater or other reference thermal power device along with the temperature differential measured across it provides a heat capacity rate of the fluid. The heat capacity rate is numerically similar to, but in lieu of, a measurement of the mass flow rate of fluid multiplied by the specific heat of the fluid. Using heat capacity rate, it is not necessary to know the specific heat of the fluid or its mass flow rate, although the specific heat and flow rate should remain relatively constant during measurement. Small changes in the specific heat of the fluid and the flow during a determination of heat capacity rate will not adversely affect the result. Large changes in specific heat or flow rate will not affect the determination of heat capacity so long as they occur over a time span longer than the time required for measurement. Inasmuch as all measurements are being made on an entire fluid stream, for example, on a single conduit, and no fluid is added or removed from the stream between the first and last temperature sensors, the specific heat and the flow rate of the fluid will be the same at all points in the monitorial section of the stream.

The methodology is to divide the amount of thermal power introduced into the stream, dQR, by the first temperature differential, (T2−T1). "dQR" may be the known or measurable amount of electric power which, obviously, is a function of voltage and current delivered to thermal power device TDR. The quotient is the heat capacity rate C.

When the temperature differential (T3−T2) across the unknown heat source or unknown heat sink is obtained by the temperature sensors T-2 and T-3, the temperature differential is multiplied by the heat capacity rate to determine the net thermal power which is added to or removed from the fluid stream in the conduit section between temperature sensors T-2 and T-3 by the unknown thermal device TDU. By knowing the heat capacity of the flowing fluid stream, when a particular temperature increase or temperature decrease is determined across an unknown source or sink, it is possible to determine exactly how much heat is added or removed from the fluid stream.

If the temperature measurement at the first temperature sensor T-1 is T1, the temperature measured by the second temperature sensor T-2 is T2, and the third temperature measured by the third temperature sensor T-3 is T3, then the thermal power contribution is represented by the equations:

(1) Determination of heat capacity rate is:

$$C = \frac{dQR}{T2 - T1}, \text{ or in}$$

the specific embodiment where TDR is an electrical resistance heater;

$$C = \frac{P}{T2 - T1},$$

where P is the electrical power provided to the heater.

(2) Determination of thermal power contribution dQU is:

$$dQU = C(T3 - T2).$$

(3) In a combined form, means hereinafter described solves the equation:

$$dQU = dQR \frac{(T3 - T2)}{(T2 - T1)}.$$

Importantly, the monitor of this invention does not require knowledge of flow rate and the specific heat of the fluid. Further, it does not matter if the fluid stream contains solid or particulate matter. It is, of course, desirable to have the fluid stream relatively homogeneous, at least between the various temperature sensors during any particular thermal power contribution measurement, and the homogeneity changes should be slower than the response time of the equipment. A microprocessor can be used to average out differences in the homogeneity of the matter in the fluid stream.

The temperature differences which may be used for efficient operation can even be quite small, for example, on the order of 0.5 degrees C. In many cases the device may be operated with temperature differences on the order of about 1 degree C.

It is also possible to measure other forms of energy or power which may be added to or removed from the fluid stream. For example, the thermal power monitor of the present invention can be used to measure the rise in the internal energy of an adiabatic fluid stream which may result, for example, from a flow restriction causing a drop in the stream's pressure energy. This is effective for non-intrusive trouble-shooting of fouled piping systems and the like. For example, it has been determined that a four atmosphere pressure drop (60.7 pounds per square inch) in a stream of water will give rise to about 0.1° C. temperature differential. It has also been found that the thermal power monitor of the present invention is able to determine temperature rises corresponding to pressure drops as low as 2.5 p.s.i. and of 10 to 60 p.s.i. with fairly good accuracy.

FIGS. 2 and 3 illustrate alternate arrangements of a thermal power monitor of the present invention with respect to one or more unknown thermal power sources or thermal power sinks. FIG. 2 illustrates an alternate arrangement using first and second temperature sensors T-1 and T-2 across the thermal reference device TDR, but in this case a pair of independent temperature sensors T-3 and T-4 are located across unknown power sink source or sink TDU.

FIG. 3 illustrates an embodiment in which two unknown thermal power sources or thermal power sinks, namely, TDU-1 and TDU-2, may be used for monitoring thermal power addition or thermal power extraction from a fluid stream. In this case, first unknown thermal power source or sink TDU-1 has the temperature differential across the fluid measured by temperature sensors T-3 and T-4. The second unknown thermal power source or thermal power sink TDU-2 has the temperature differential across it measured by temperature sensors T-5 and T-6. Thus, it is possible to determine the amount of thermal power added to or removed from the stream by each of these two unknown sources or sinks independently. Further, by determining the temperature differential between T-3 and T-6, it is possible to determine the overall thermal power contribution from both unknown sources or sinks. It is also possible to determine the entire contribution to or from the fluid stream including that provided by thermal reference device TDR by determining the temperature differential from the sensor T-1 across the system to the temperature sensor T-6 as the second temperature differential.

The unknown thermal power contribution, for example, the unknown thermal power addition by each unknown source or sources, or the unknown thermal power drain by each sink or sinks, or combinations thereof, in the embodiments illustrated in FIGS. 2 and 3, is determined in the same manner as the embodiment of FIG. 1. In each case the pertinent temperature differential is multiplied by the determined heat capacity rate.

FIG. 4 illustrates a more preferred embodiment of the thermal power monitor of the present invention in which an unknown amount of thermal power is added to or removed from the fluid stream in the conduit or line 14 by means of an unknown energy sink or energy source TDU. In this case, reference is made to the amount of thermal power as the actual physical parameter which is measured by the monitor of the invention. Thermal energy added to or removed from the fluid stream may be determined by measuring the power over a specific time duration at a specific power level.

In the embodiment of the invention illustrated in FIG. 4, the heat reference means or device TDR is a heater 15 which provides a known amount of thermal power (heat) introduced into the fluid stream. Heater 15 includes an inner sheath 16 of flexible, dielectric material that imbeds alloy heating coils 18 supplied with electrical energy through lines 20. Sheath 16 is preferably thin, flexible, and formed of a dielectrical material, for example, it may be silicone based. It has a parting line 22 to permit its application to line 14.

An insulation jacket 24 encases the sheath and overlaps its ends. This jacket also is split and has a parting line 26. The insulation is sufficient to avoid material heat loss to the environment, either radially of the heater or upstream or downstream of heater 15. The insulation assures that the heat energy from heater 15 is essentially completely introduced into the fluid flowing through line 14 within tolerable bounds.

A flexible cover 28 encases insulation jacket 24 and includes means for securely attaching the heater to conduit 14. These means include hook and pile type fasteners. Specifically, a set of four mating hook and pile type fasteners 32, 34, 36 and 38 of the cover cooperate to secure the cover, insulation and heater sheath firmly to conduit 14. The outer surface of cover 28 has a radiation shield 29 of metal foil that isolates the conduit 14 in the zone of the heater from environmental radiation.

Three temperature sensing units are also used. The first of these is upstream of the heater and is indicated by reference numeral 40. This unit 40 includes insulation 42 and a temperature probe 44 adapted to rest against a surface of the conduit 14. Hook and pile fasteners 46 secure the insulation and probe to conduit 14. A downstream temperature sensing unit 50 is of basically the same construction. It has a temperature probe 52 backed by insulation 54, the entire unit being securable to conduit 14 by hook and pile fasteners 56. A third temperature sensor is shown at 60 and it again includes a temperature sensor probe 62 backed by insulation 64 and attachable to conduit 14 through hook and pile fasteners 66.

A control console 70 (to be described in some detail subsequently) provides for the integration of the heat input or extraction information with the knowledge of the heat input or removal by unknown source or sink TDU. It may also contain amplifier, offset, and feedback circuitry, if required, to effect accurate temperature sensing.

Preferably, the heating sheath is of a silicone rubber material with so-called "Cupron" wire conductors. These "Cupron" wire conductors are formed of an alloy of aobut 45% nickel and 55% copper and offered by the Amax Specialty Metals Corp. (formerly Wilbert B. Driver Company) of Parsippany, N.J. The Cupron wire is designed to have a resistance of 15 ohms and therefore a unit rating of 666 watts when used with a 100 volt power source. This particular type of wire has an electrical resistance which is not very temperature sensitive, and thus has a substantially constant electrical resistance over a wide temperature range. This permits an easy correlation of electrical power consumption and thermal power transfer and a single electrical parameter, for example, current or voltage supplied to the heater. The thinness of the silicone rubber and the flexibility of the wire allow the unit to make excellent thermal contact with the line or conduit 14 when held in place by the insulation jacket and sleeve.

A thermal power meter constructed in accordance with the principles of this invention has an accuracy within plus or minus 3% over a wide range of flow rates and energy input rates from the unknown source. The unit is lightweight and obviously very easy to use. It is extremely versatile in that the unit can be strapped to various sized pipes in a matter of a few seconds. The insulation jacket is of simple design and can be mounted quickly merely by placing its halves over the pipe.

Accuracy of the system was determined to be only weakly dependent on the mass flow rate of the fluid being monitored and more strongly related to the energy or thermal power output or drain by the unknown source or sink.

The location of the temperature sensors on either side of the heating unit affects the accuracy of the meter. The closer the sensors are to the heater, the greater the effect the mass flow rate of the fluid has on meter accuracy. For example, in one test when the temperature sensors were moved to a distance of six inches from the heater on a one-inch line it was found that the accuracy was only plus or minus 10%.

The thermal response time of the system is comparatively rapid. It depends upon flow rate and heater insulation. A temperature sensor backed by a 1¼ inches thick insulation needs about 5 to 7 minutes to achieve 95% of the equilibrium temperature of the pipe. This lag time can induce error. Response time can be reduced by improving the heat transfer from the fluid to the temperature sensors and by making the mass and thickness and heat capacity of the sensors and the associated insulation small.

The temperature sensor position with respect to the heater was found to have an effect on accuracy because of two conditions: (1) heat conduction up and down the line, and (2) poor thermal mixing downstream in the heated fluid. These effects are greatest at low Reynolds numbers. It is found that for a horizontal line with a Reynolds number of 6,000, temperature sensor positions 20 diameters from the heater virtually eliminated these problems. A downstream deviation of about 3% occurred at a little less than 10 diameters. The upstream deviation is less sensitive.

The insulation is important to avoid environmentally induced errors. Tests reveal that diurnal air temperatures and radiation variations have an effect on what the sensors detect as temperature. In one instance it was found that one of the sensors in close proximity to the metal shall of the test stand experienced a 0.1° C. shift in temperature compared to the other two sensors. This was due to the radiation and convective heat input from the metal test stand to the sensor. It is preferable to avoid this effect by utilizing radiation shields between the environment and the sensors. The shield can be placed on the outside of the insulation and, for example, may take the form of metal foil.

Temperature sensing circuitry should have a high sensitivity and should be well matched to reduce the amount of heat energy that is necessary for the heater to supply. Satisfactory sensitivity is within 0.001° C., and can be met by probes manufactured by Analog Devices, having model number AD-590, in conjunction with the electronic circuitry hereinafter described. The probe downstream of the unknown source, or sink TDU, namely probe 62, and its associated circuitry would not have to be as sensitive if the temperature rise between probe 52 and probe 62 is 5 to 50 times as great as between probes 44 and 52. A sensitivity for the third sensor and its associated circuitry of 0.01° C. is satisfactory to accurately determine this large temperature differential.

With reference to FIG. 5, a line schematic of the electrical aspects of one embodiment of the invention is presented. An upstream temperature sensor 100, corresponding to sensor 44, is in circuit with a power supply and an operational amplifier 102. Specifically, the sensor is in circuit with a negative side of the power source 104 and an input to the amplifier. The power supply must be accurately controlled to avoid line voltage fluctuations that would affect the accuracy of the monitor. The amplifier circuit itself is standard. It is used to convert the current controlled signal from the sensor into an adjustable voltage signal. It includes a lead 106 from the sensor, a lead 108 from the positive side of the power source, and a lead 110 from the negative side. An input to the amplifier is connected to ground potential through a resistor 112. A capacitor 114 is connected across the amplifier 102 as shown. The output of the amplifier 102 goes through a line 116 to a line 118. A resistor 120 is between the output of the amplifier and the negative side of the power supply. The output of the amplifier is indicated at VT-1.

The gain of the amplifier circuit is adjusted in a feedback branch circuit 122. The circuit includes a variable resistor 124 in series with a resistor 126 to the line 118. Variable resistor 130 from a voltage regulator 131 couples into the circuit of variable resistor 124 and resistor 126 where they join the signal input of amplifier 102 at line 133. The voltage regulator may be at a potential of 2.5 volts. The voltage through the circuit of these variable resistors and resistors is also adjustable by a potentiometer 132 between them and ground. This potentiometer is mounted on the outside of the cabinet containing this electronic circuitry so as to be easily adjusted externally. Both the circuits with variable resistor 130 and potentiometer 132 control the offset voltage produced by amplifier 102.

A scaling or voltage dividing circuit develops a voltage signal VT-0.01. This circuit consists very simply of a resistance 140 from the output of amplifier 102 in series with a variable resistor 142 and ground. The signal is taken off at line 144 and may be one hundredth the strength of the signal VT-1.

The circuits for the other two sensors corresponding to the downstream temperature sensor from the heater and the downstream temperature sensor from the unknown energy source or sink are shown at reference numerals 160 and 162 and are identical to the circuit described with reference to sensor 100 except that the circuit of sensor 160 does not have an external fine adjustment. The external fine adjustment for circuit 162 is indicated at 163 and corresponds to potentiometer 132. Sensor 160 corresponds to sensor 52 and sensor 162 corresponds to sensor 62. Because of the identity of the circuits for these sensors they will not be further described except to note that the output of sensor 160 is VT-2 and VT-0.02, and the output of sensor 162 is VT-3 and VT-0.03.

A signal VT-S representing the difference between the temperature sensed at 162 and the temperature sensed by sensor 160 times an appropriate scale factor (k) which is dependent upon the known reference power input to the fluid stream is scaled in a branch circuit 164. That circuit includes a resistance 168 and a variable resistor 170 in series. The scale signal representing the difference of these two temperatures comes off at line 174 between resistance 168 and 170. This signal is a potential relative to ground of a value (VT-2)+k[(VT-3)−(VT-2)].

A rotary switch 180 couples the output of the sensors and their amplifier scaling circuits to a digital voltmeter 182.

Digital voltmeter 182 has four variable voltage input portions which control the numeric indication on a liquid crystal display 183. These are: IN HI, IN LO, REF HI and REF LO. The number displayed on the liquid crystal display is the numerical value of the ratio of the potentials (IN HI−IN LO)/(REF HI−REF LO). Rotary switch 180 applies the different signals to digital voltmeter inputs to produce the desired ratios, differences, and values. Six positions of the switch are indicated by numerals 1 through 6. In a first position, VT-S goes to IN HI, VT-2 to IN LO and REF HI, while VT-1 goes to REF LO. Digital voltmeter 182 then displays [(VT-S)−(VT-2)]/[(VT-2)−(VT-1)], which equals k [(VT-3)−(VT-2)]/[(VT-2)−(VT-1)]. This signal is the actual thermal energy rate (thermal power) into the fluid stream between sensors 160 and 162 when the scale factor (k) has been appropriately determined by resistances 168 and 170.

For displaying temperature differences useful to finely adjust the device by potentiometers 163 and 132, second and third positions are used. In the second position [(VT-2)−(VT-3)]/1.00 is displayed, with the 1.00 coming from circuit 185 where a variable resistor 186 is in series with a resistor 187 and a constant voltage, for example, a battery 188. The variable resistor 186 has its tap 190 adjusted for 1.00 volts above the potential at 189, the potential at REF LO. In the third position all is the same except VT-3 is switched to IN HI in the place of VT-2.

To make each of the three sensors read the same temperature, they are all put at the same temperature for ten minutes, then the second position is selected and variable resistor 132 adjusted until the display reads zero; then the third position is selected, and variable resistor 163 is adjusted until the display reads zero.

The individual temperatures of sensors 100, 160, and 162 can be displayed by using switch positions 4, 5 and 6, respectively. In these positions VT0.01, VT0.02 and VT0.03 are switched into IN HI, ground to IN LO and 1.00 is put between REF HI and REF LO. Then the display indicates the value of the signals VT0.01, VT0.02 and VT0.03, respectively.

The auxiliary circuitry associated with the digital voltmeter is used for its functioning, but it is completely standard and will not be described further, except for the filter produced by the connection of a capacitor 197 and a resistor 195 in parallel between the COM port on the digital voltmeter and IN LO. This filter reduces instabilities found on switch positions 1, 2 and 3.

The thermal power monitor can be made to totalize the amount of sensible heat energy which flows into the fluid stream by using, in series, an analog arithmetic division circuit to produce the [(VT-S)−(VT-2)]/[(VT-2)−(VT-1)] signal, then a voltage-to-frequency converter to produce a pulse train whose frequency is a direct and adjustable function of its input voltage, and finally a pulse counting circuit to record each pulse. This is equivalent to recording each unit of energy which flows into or out of the fluid stream between sensors 162 and 160.

The system could obviously be easily modified to include its reference power input into its total power indication, by switching the connection at 164 (to VT-2) on to VT-1 at 118, and also changing the IN LO signal when on position 1 of the rotary switch to VT-1 from VT-2. Then the display would be k[(VT-3)−(VT-2)]/[(VT-2)−(VT-1)]+k ideally, which equals the displayed k [(VT-3)−(VT-1)]/[(VT-2)−(VT-1)]. For example, this modification is effective when using embodiments as illustrated and described in connection with FIGS. 1, 2 and 3. Thus, this modification shows the simplicity involved in looking at power contribution using various sensor arrangements and arrangements of unknown sources and sinks.

Figure 6:
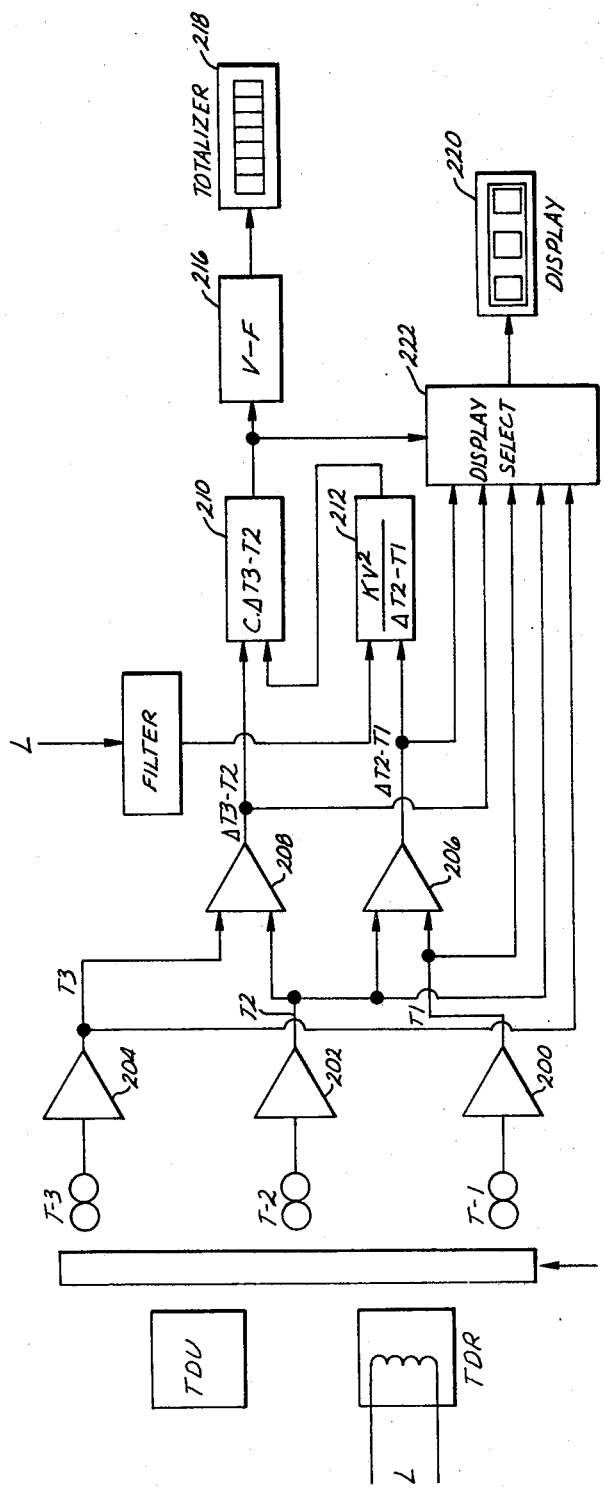
FIG. 6 is an alternate embodiment of an electrical circuit for providing totalizing information.

FIG. 6 illustrates one embodiment of an electrical circuit which is capable of providing total information with regard to thermal power contribution from an unknown source or an unknown sink. In this embodiment of the invention, the signals generated at each of the three temperature sensors, T-1, T-2 and T-3 are amplified by respective amplifiers 200, 202 and 204 which receive the signals from the three sensors. A thermal reference device TDR, namely a heater, is powered by a line voltage L to operate a resistive element of the heater for generating heat.

The amplified signals from the three sensors are introduced into differential amplifiers 206 and 208, in the manner as illustrated, for purposes of removing spurious noise from the amplified signals and to also provide for common mode rejection. The output of the differential amplifier 208, which effectively represents the differential temperature signal T3−T2, is introduced into a multiplier 210 which multiplies this signal by the determined heat capacity rate C, as hereinafter described in more detail. This heat capacity rate C is provided from the output of a divider circuit 212. The divider circuit effectively receives the signal from the output of the differential amplifier 206 and which is, in effect, the differential temperature signal T2−T1. Further, this differential temperature signal T2−T1 is divided into the square of the line voltage L which is also multiplied by a constant k representative of the heater TDU and this output of the divider circuit 212 provides the heat capacity rate constant C.

The output of the multiplier circuit 210 is introduced into a voltage-to-frequency converter 216 which converts the output to a frequency form capable of operating a totalizer 218 for thereupon displaying the total thermal power contribution.

It is also possible to obtain an instantaneous display of this information by means of a conventional display member 220. Outputs of both the differential amplifiers 206 and 208, as well as the individual amplifiers 200, 202, and 204 are introduced into a display select circuit 222, and the display select circuit 222 has an output for controlling the display member 220 in the manner as illustrated. In the circuit of FIG. 6, differential amplifier 208 preferably may have a unity gain, and amplifier 206 may have a gain in the range of about 15 to 20. The gains of the amplifiers are adapted to scale the output signals to the desired operating ranges of the multiplier 210 and multiplier-divider 212. Multiplier 210 and the multiplier-divider circuit 212, together with the voltage-to-frequency converter 216 and the totalizer 218, integrate the time rate of the rate of the net thermal energy contribution in order to provide a total amount of thermal energy contribution that is the amount of thermal energy either added to or removed from the fluid stream.

This invention provides a unique and novel non-intrusive thermal power transfer apparatus and method which permits determination of heat loss or heat gain with respect to a moving fluid stream.

The present invention has been described with reference to certain preferred embodiments. The spirit and scope of the appended claims should not, therefore, necessarily be limited to the foregoing description.

What is claimed is:

1. An improved non-intrusive thermal power monitor for determining thermal power contribution to a fluid stream from an unknown thermal power source or sink, the monitor comprising:
   (a) thermal power reference device means adapted to add or remove a known amount of heat to or from a fluid stream flowing through a fluid carrying conduit without intruding into the fluid or conduit;
   (b) first non-intrusive temperature differential measuring means for measuring a first temperature differential across the power reference device and generating an electrical signal which is a function of the first temperature differential, the first non-intrusive temperature differential measuring means including a first temperature sensor and a second temperature sensor, each such temperature sensor having means to permit its attachment to the conduit at least ten conduit diameters from the thermal power reference device;
   (c) second non-intrusive temperature differential measuring means for measuring a temperature differential across a portion of the fluid stream that contains an unknown thermal power source that adds thermal power to the stream or an unknown thermal power sink that extracts thermal power from the stream, the second temperature differential measuring means generating an electrical signal which is a function of the second temperature differential;
   (d) means for determining the heat capacity rate of the fluid from the first temperature differential signal and the known amount of heat; and
   (e) means for determining the thermal power introduced into or removed from the fluid by the unknown source or sink from the heat capacity rate and the second temperature differential signal.

2. The improved non-intrusive thermal power monitor claimed in claim 1 wherein the thermal power reference device is a heater which adds a known amount of heat to the fluid stream.

3. The improved non-intrusive thermal power monitor claimed in claim 1 wherein the monitor is constructed so that fluid flows first through the power transfer device before flowing through the unknown power sink or unknown power source.

4. The improved non-intrusive thermal power monitor claimed in claim 2 wherein the heater is an electrically operable heater where the amount of heat applied to the fluid is proportional to the amount of current, or voltage, or electrical power used to provide such heat, and the current, or voltage, or electrical power provides a measure of the amount of heat applied.

5. The improved non-intrusive thermal power monitor claimed in claim 1 wherein the monitor includes a third temperature differential measuring means for measuring a third temperature differential across and obtaining a third electrical signal representative of thermal power added to or removed from the fluid stream by means of a second unknown thermal power source or sink, and the thermal power determining means receives the third electrical signal and determines the thermal power contribution to or from the fluid stream by the second unknown thermal power source or sink.

6. The improved non-intrusive thermal power monitor of claim 2 including means for obtaining an electrical reference signal from the known amount of heat and wherein the thermal power determining means is adapted to divide the electrical reference signal by the electrical signal that is a function of the first temperature differential.

7. The improved non-intrusive thermal power monitor claimed in claim 1 wherein the thermal power applied to or removed from the fluid by the unknown source or sink is acquired by multiplying the heat capacity rate by the signal that is a function of the second temperature differential.

8. The improved non-intrusive thermal power monitor claimed in claim 1 wherein the means for determining the thermal power provides instantaneous measurements of thermal power contribution from the unknown source or sink.

9. The improved non-intrusive thermal power monitor claimed in claim 1 wherein the means for determining the thermal power provides a total measurement of thermal power contribution from the unknown source or sink on a time basis.

10. A non-intrusive thermal power measuring apparatus for determining thermal power added to or taken from a fluid stream by a thermal power source or thermal power sink comprising:
   (a) reference heat application means for applying a known amount of heat to a fluid passing through a fluid carrying conduit and for obtaining a signal representative of the known amount of heat;
   (b) a first temperature sensor for measuring a fluid temperature on one side of the reference heat application means with respect to the direction of fluid flow and generating a first electrical signal in response thereto and as a function of the measured temperature, the first temperature sensor including a probe and means on such probe to permit its attachment to the conduit at least ten conduit diameters upstream of the heat application means;
   (c) a second temperature sensor for measuring the fluid temperature on the opposite side of the heat application means with respect to the direction of fluid flow and generating a second electrical signal in response thereto and as a function of such measured temperature, the second temperature sensor including a probe and means on such probe to permit its attachment to the conduit at least ten conduit diameters downstream of the heat application means;
   (d) a third temperature sensor for measuring fluid temperature at the opposite side of said power source or thermal power sink with respect to either of the first or second temperature sensors and generating an electrical signal representative of and a function of the temperature measured thereby;
   (e) thermal power determining means including means for subtracting the first signal from the second signal to obtain a temperature differential signal, dividing the temperature differential signal into the signal representative of the known amount of heat to derive a heat capacity rate of the fluid, using the third temperature signal to obtain an unknown source or sink temperature difference signal, and multiplying that temperature difference signal by the heat capacity rate to determine the thermal power contribution provided by the unknown thermal power source or sink.

11. The non-intrusive thermal power measuring apparatus claimed in claim 10 wherein the thermal power determining means uses the second and third electrical signals to determine a temperature difference across the unknown thermal power source or sink.

12. The non-intrusive thermal power measuring apparatus claimed in claim 10 including a fourth sensor located on an opposite side of the unknown source or sink with respect to the third sensor for providing a fourth electrical signal representative of a temperature difference across the unknown source or sink.

13. The non-intrusive thermal power measuring apparatus claimed in claim 10 wherein the first temperature sensor is upstream of the heat application means, the second temperature sensor is downstream of the heat application means and upstream of the power source or power sink, and the third temperature sensor is downstream of the power source or power sink.

14. The non-intrusive thermal power apparatus claimed in claim 10 wherein the heat application means is an electrically operable heater where the amount of heat applied to the fluid is proportional to the amount of current, or voltage, or electrical power used to provide such heat, and the current, or voltage, or electrical power provides the measure of the amount of heat applied.

15. The non-intrusive thermal power apparatus claimed in claim 10 wherein the first, second and third temperature sensors each have a temperature probe adapted to be attached to the conduit and insulation surrounding a portion of each probe to isolate it from the environment.

16. The non-intrusive thermal power apparatus claimed in claim 10 including amplifier means for multiplying the signals from the temperature sensors.

17. The apparatus claimed in claim 10 or 11 wherein the third temperature sensor includes a probe and means on such probe to permit its attachment to the conduit at least ten conduit diameters from the power source or thermal power sink.

18. The apparatus of claim 10 wherein
   (a) the means on the probe of the first temperature sensor permits its attachment to the conduit at least twenty conduit diameters upstream of the heat application means; and
   (b) the means on the probe of the second temperature sensor permits its attachment to the conduit at least twenty conduit diameters downstream from the heat application means.

19. The apparatus claimed in claim 17 wherein the sensitivity of the first and second temperature probes is at least about 0.001° C.

20. The apparatus claimed in claim 19 wherein the third temperature sensor has a probe with a sensitivity of at least about 0.01° C.

21. The apparatus claimed in claim 10 wherein the attachment means for the probes each includes a jacket of hook and pile fastener means and insulation means inside the jacket to isolate each probe from the environment.

22. An improved, non-intrusive meter for determining the energy or power contribution to a fluid stream from a source or sink comprising:
   (a) a heater adapted for attachment to a line through which the fluid stream is passing, the heater including an electrical heating element, insulation backing the heater element to prevent heat loss to the environment, and means for attaching the heater to the line;
   (b) a first temperature sensor including a temperature probe adapted to be attached to the line upstream from the heater to obtain a first temperature signal, the first temperature sensor having insulation to isolate its probe from the environment;
   (c) a second temperature sensor including a temperature probe adapted to be attached to the line downstream of the heater and upstream from the source or sink to obtain a second temperature signal, the second temperature sensor having insulation to isolate its probe from the environment;
   (d) a third temperature sensor including a temperature probe adapted to be attached to the line downstream from the source or sink to obtain a third temperature signal, the third temperature probe having insulation to isolate its probe from the environment;

(e) means for providing a signal representative of an amount of energy or power supplied by the heater to the stream;

(f) means to obtain a first temperature difference signal across the unknown source of the second and third temperature signals;

(g) means to obtain a second temperature difference signal across the heater of the first and second temperature signals; and (h) means for multiplying the energy or power signal by the first temperature difference signal across the unknown source or sink and dividing that product by the second temperature signal difference across the heater to obtain the energy or power contribution or drain to the fluid stream from the source or sink.

23. The improvement of claim 22 including means to amplify the first, second and third signals.

24. The improvement of claim 23 including means to amplify the difference between the first and second signals and means to amplify the difference between the second and third signals.

25. The improvement of claim 22 wherein the means for providing a signal representative of an amount of energy or power is the heater which is adapted to provide a constant amount of energy or power.

26. The improvement of claim 22 wherein the means for providing a signal representative of an amount of energy or power is means for measuring the current or voltage or power applied to the heater.

27. The improvement claimed in claim 22 including:

(a) means on the first temperature probe to permit its attachment to the line at least ten line diameters upstream of the heater; and (b) means on the second temperature probe to permit its attachment to the line at least ten line diameters downstream from the heater.

28. A method for non-intrusively measuring the amount of thermal power contribution to or from a fluid stream flowing in a conduit, the method comprising:

(a) supplying or removing a known amount of heat to a flowing fluid stream by or from a reference heat means without intrusion into the fluid stream and obtaining a reference electrical signal thereof;

(b) measuring a first temperature of the fluid stream at least ten conduit diameters from the reference heat means without intrusion into the fluid stream and generating a first electrical signal in response thereto;

(c) measuring a second temperature of the fluid stream without intrusion into the fluid stream on the opposite side of the reference heat means and at least ten conduit diameters from such heat means and generating a second electrical signal in response thereto;

(d) taking the difference between the first and second electrical signals to provide a temperature differential signal across the reference heat means;

(e) measuring a third temperature of the fluid stream with respect to an unknown thermal power source which adds thermal power to the stream or an unknown thermal power sink which removes thermal power from the fluid stream and generating a third electrical signal in response thereto;

(f) electrically determining the heat capacity rate from the temperature differential signal and the reference signal of the amount of heat provided by or removed by the reference heat means; and (g) determining the amount of thermal power added to or removed from the fluid stream by the unknown source or sink using the third electrical signal and the heat capacity rate.

29. The method of claim 28 wherein the first electrical signal is subtracted from the second electrical signal to provide a temperature differential signal and this last named temperature differential signal is electrically divided into a signal representing the heat applied to or removed from the fluid stream by the reference heat means to thereby determine the heat capacity rate.

30. The method of claim 29 wherein the third electrical signal is used with another electrical signal to provide a signal representative of a differential temperature measurement and this last named signal is electrically multiplied by the heat capacity rate to determine the amount of thermal power added to or removed from the fluid stream by the unknown source or sink.

* * * * *